US012702724B2

(12) United States Patent
Barfett

(10) Patent No.: US 12,702,724 B2
(45) Date of Patent: Aug. 11, 2026

(54) SYSTEM AND METHOD FOR DISINFECTING A VOLUME IN SPACE

(71) Applicant: Neuraviolet Inc., London (CA)

(72) Inventor: Joseph John Barfett, London (CA)

(73) Assignee: Joseph John Barfett Medicine Professional Corporation, Toronto (CA)

( * ) Notice: Subject to any disclaimer, the term of this patent is extended or adjusted under 35 U.S.C. 154(b) by 738 days.

(21) Appl. No.: 17/920,585

(22) PCT Filed: Apr. 23, 2021

(86) PCT No.: PCT/CA2021/050556
§ 371 (c)(1),
(2) Date: Oct. 21, 2022

(87) PCT Pub. No.: WO2021/212231
PCT Pub. Date: Oct. 28, 2021

(65) Prior Publication Data
US 2023/0149582 A1 May 18, 2023

Related U.S. Application Data

(63) Continuation-in-part of application No. PCT/CA2020/051635, filed on Nov. 27, 2020.
(Continued)

(51) Int. Cl.
*A61L 2/24* (2006.01)
*A61L 2/084* (2026.01)
(Continued)

(52) U.S. Cl.
CPC ................ *A61L 2/24* (2013.01); *A61L 2/084* (2013.01); *A61L 2/10* (2013.01); *A61L 9/20* (2013.01);
(Continued)

(58) Field of Classification Search
CPC .......... A61L 2/10; A61L 9/20; A61L 2202/14
See application file for complete search history.

(56) References Cited

U.S. PATENT DOCUMENTS 9,061,083 B2 6/2015 Chu et al.
9,603,960 B2 3/2017 Dobrinsky et al.
(Continued)

FOREIGN PATENT DOCUMENTS

CA 2835661 A1 10/2012
CA 2873550 A1 7/2013
(Continued)

OTHER PUBLICATIONS

International Search Report and Written Opinion dated Feb. 16, 2021 on PCT/CA2020/051635.
(Continued)

*Primary Examiner* — Donald R Spamer
*Assistant Examiner* — Kayla Rose Sarantakos
(74) *Attorney, Agent, or Firm* — Brunet & Co. Ltd.; Robert Brunet; Hans Koenig

(57) ABSTRACT

A method and system for disinfecting a volume in space involves: localizing a volume in space requiring disinfection; calculating directions to the volume in space from a plurality of available beam-producing light sources for disinfection and projecting at least one light beam from the available beam-producing light sources to the volume in space; and, coordinating the projected light beams to minimize time required to deliver a threshold disinfecting light dose to the volume in space requiring disinfection.

22 Claims, 4 Drawing Sheets

Related U.S. Application Data

(60) Provisional application No. 63/015,066, filed on Apr. 24, 2020.

(51) Int. Cl.
*A61L 2/10* (2026.01)
*A61L 9/20* (2006.01)
*A61L 103/75* (2026.01)

(52) U.S. Cl.
CPC ........ *A61L 2103/75* (2026.01); *A61L 2202/11* (2013.01); *A61L 2202/14* (2013.01); *A61L 2209/111* (2013.01); *A61L 2209/12* (2013.01)

(56) References Cited

U.S. PATENT DOCUMENTS 9,707,307 B2 7/2017 Shur et al.
9,878,061 B2 1/2018 Shur et al.
10,071,262 B2 9/2018 Randers-Pehrson et al.
10,369,379 B2 8/2019 Randers-Pehrson et al.
10,512,704 B2 12/2019 Dytioco et al.
10,517,976 B2 12/2019 Shur et al.
10,960,091 B2 3/2021 Dijkstra et al.
11,992,564 B2 5/2024 Dijkstra
2011/0054574 A1 3/2011 Felix
2014/0060096 A1 3/2014 Shur et al.
2015/0073396 A1 3/2015 Randers-Pehrson et al.
2015/0265346 A9 9/2015 Randers-Pehrson et al.
2016/0271803 A1 9/2016 Stewart
2017/0246331 A1* 8/2017 Lloyd .................... A61Q 17/04
2018/0117189 A1 5/2018 Yadav et al.
2018/0118337 A1 5/2018 Viel
2018/0185527 A1 7/2018 Lalicki et al.
2019/0022263 A1 1/2019 Quilici
2019/0117809 A1* 4/2019 Katz ...................... G06V 20/52
2019/0117812 A1 4/2019 Olsen et al.
2019/0262097 A1 8/2019 Armour et al.
2020/0078483 A1 3/2020 Eidman
2020/0101183 A1 4/2020 Dijkstra et al.
2021/0290814 A1* 9/2021 Waterbury ................ A61L 2/10
2024/0207475 A1* 6/2024 Kaler ........................ A61L 9/20

FOREIGN PATENT DOCUMENTS

CN 202125089 1/2012
CN 203588504 5/2014
CN 107439511 A 12/2017
CN 109587327 A 4/2019
CN 208705724 4/2019
CN 208852057 5/2019
CN 110251698 A 9/2019
CN 210140075 3/2020
CN 111001025 A 4/2020
JP 2020010820 1/2020
KR 20180017756 2/2018

OTHER PUBLICATIONS

International Search Report and Written Opinion dated Jul. 21, 2021 on PCT/CA2021/050556.
Billboard Advertising by LaserWorld, Aug. 20, 2020.
U.S. Appl. No. 63/015,468, filed Apr. 24, 2020, which is a priority document of US 2024/0207475.
U.S. Appl. No. 63/002,184, filed Mar. 30, 2020, which is a priority document of US 2024/0207475.
U.S. Appl. No. 62/993,546, filed Mar. 23, 2020, which is a priority document of US 2024/0207475.
Office action dated Jun. 2, 2025 on U.S. Appl. No. 17/920,565.
Office action dated Oct. 16, 2025 on U.S. Appl. No. 17/920,565.

* cited by examiner

SYSTEM AND METHOD FOR DISINFECTING A VOLUME IN SPACE

CROSS-REFERENCE TO RELATED APPLICATIONS

This application is a national entry of International Patent Application PCT/CA2021/212231 filed Apr. 23, 2021, which is a continuation-in-part of International Patent Application PCT/CA2020/051635 filed Nov. 27, 2020 and claims the benefit of United States Provisional Patent Application U.S. Ser. No. 63/015,066 filed Apr. 24, 2020, the entire contents of all of which are herein incorporated by reference.

FIELD

This application relates to disinfection systems and methods, more particularly to radiation-based disinfection systems and methods utilizing beams of radiation, especially with computer guidance.

BACKGROUND

Electromagnetic radiation and particularly blue light and ultraviolet (UV) light has the potential to be used as a disinfectant if applied at an appropriate dosage (i.e., power level, exposure time, pulse train characteristics, frequency/wavelength). Of the UV wavelengths, UV-C is most potent as a disinfection tool, but can also be potentially toxic especially to skin or vulnerable organs such as the eyes, depending on specific wavelength. Ultra-short wavelengths of UVC light for example 222 nm light may be less toxic than conventional UVC light, however these low wavelengths are also usually less effective at any given dose and require more energy deposition to accomplish a disinfection.

A variety of UV sources, most commonly incoherent sources such as lamps or light emitting diodes, have been implemented as disinfection tools, sometimes positioned by robots and sometimes controlled with motion sensors or computer algorithms, including neural networks. In general, these solutions lack the ability to disinfect spatial volumes in an intelligent fashion, especially spatial volumes of limited size, because the UV light is either only directable at specific surfaces of objects or cannot be limited to small volumes of space. In general, when people interact with an environment through breathing, aerosolized germs are most concentrated in close proximity to the person, and in particular the face, and are then subsequently affected by dispersion effects as a function of time. The inability to limit disinfection to small volumes in space from specific trajectories is detrimental in high traffic environments where people may be exposed to the radiation from conventional devices, or in the case of ultra-short wavelength light, the disinfection cannot be achieved quickly enough from the available light resources to protect people from interaction with infectious organisms in a timely manner. There is a lack of systems to deal with high traffic environments, where rapid and intelligent disinfection of specific volumes of space is required.

A system to deal with disinfection in high traffic environments is described in International Patent Application PCT/CA2020/051635 filed Nov. 27, 2020, the entire contents of which is herein incorporated by reference. While the system therein is suitable for many purposes, there still remains a need for a disinfection system especially useful for disinfecting air-borne transmissions of infectious organisms and in high traffic environments, where the system can more efficiently disinfect spatial volumes with UV light (e.g., conventional UV light, UVC light, short wavelength UVC light) and/or high energy visible light.

SUMMARY

A method of disinfecting a volume in space comprises: localizing a volume in space requiring disinfection; calculating directions to the volume in space from a plurality of available beam-producing light sources for disinfection and projecting light beams from the available beam-producing light sources to the volume in space; and, coordinating the projected light beams to reduce or maintain, preferably minimize, time required to deliver a threshold disinfecting light dose to the volume in space requiring disinfection.

A disinfection system comprises: a plurality of beam-producing light sources for disinfection; at least one imaging device for collecting image data in a field of view of the at least one imaging device; a relationship finder to determine relative physical positions of the beam-producing light sources and the at least one imaging device; and, a programmed controller for controlling the beam-producing light sources based on the image data collected from the at least one imaging device and from known positions and dispersion geometries of the beam-producing light sources, wherein the controller is programmed to: localize at least one volume in space requiring disinfection; calculate direction to the volume in space for each available beam-producing light source; and, coordinate at least one light beam projected from the available beam-producing light sources to the volume requiring disinfection to reduce or maintain time required to deliver a threshold disinfecting light dose to the volume in space requiring disinfection.

The system and method are particularly useful for disinfecting a volume in space, as well as surfaces of objects in or adjacent to the volume, in a high traffic environment during high traffic periods of time. Disinfection can be tuned to spatial volumes of various sizes thereby permitting tailoring of a disinfection response to only the spatial volumes in the environment requiring disinfection at any given moment in time.

Further features will be described or will become apparent in the course of the following detailed description. It should be understood that each feature described herein may be utilized in any combination with any one or more of the other described features, and that each feature does not necessarily rely on the presence of another feature except where evident to one of skill in the art.

BRIEF DESCRIPTION OF THE DRAWINGS

For clearer understanding, preferred embodiments will now be described in detail by way of example, with reference to the accompanying drawings, in which.

DETAILED DESCRIPTION

Figure 1:
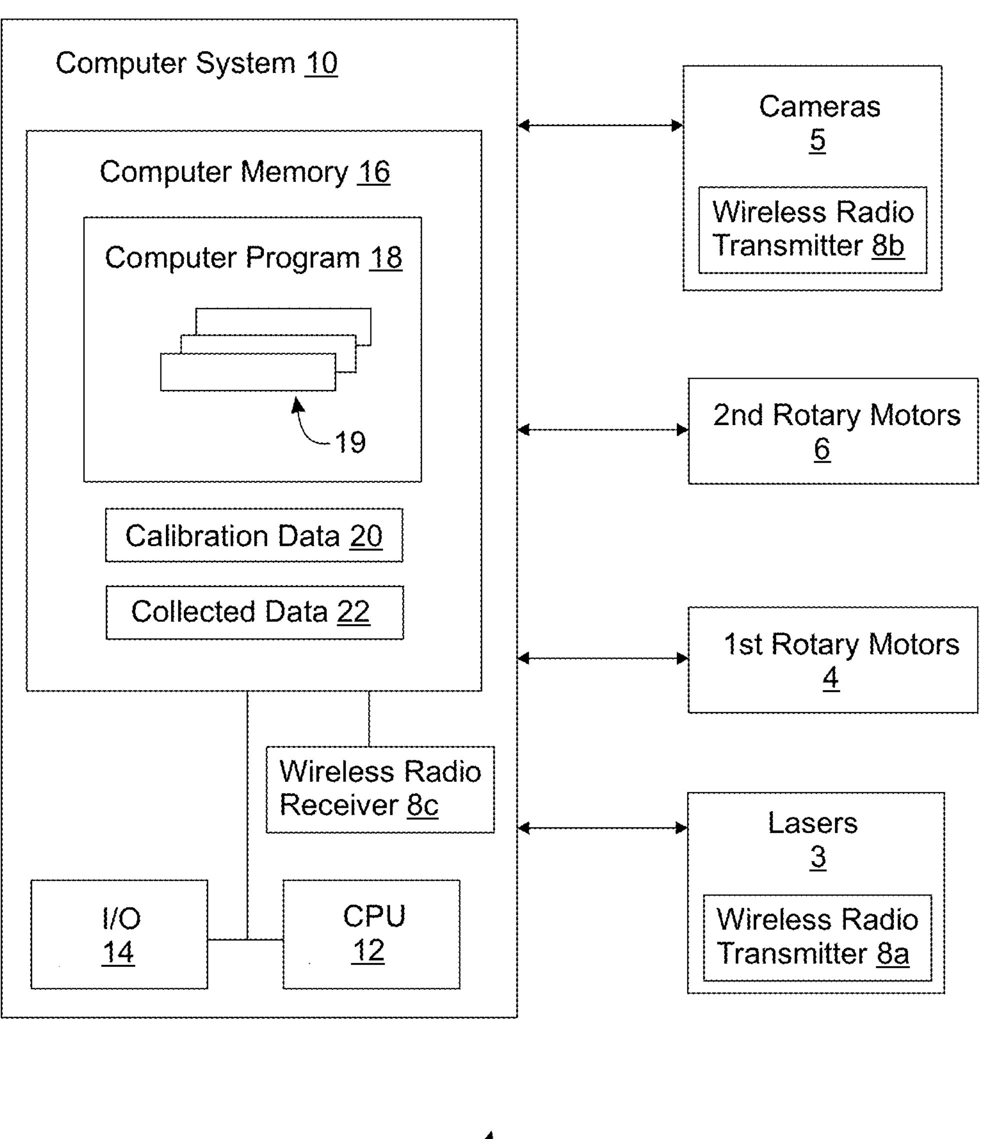
FIG. 1 depicts a block diagram of a laser-based disinfection system for disinfecting volumes in space.

The disinfection system and method are used to dynamically disinfect volumes in space in various environments to be protected. Some examples of environments to be protected include rooms or sub-regions of rooms in hospitals, airports, office buildings, retail businesses, factories, residences and the like. The system is well suited for high traffic environments, for example hospital waiting rooms and surgeries, storage rooms, airport lounges, elevators, foyers in office buildings, display spaces in retail outlets, factory floors and the like. The system and method are tunable to be able to disinfect volumes of various sizes. Tunability of spatial volume size to be disinfected is particularly important for disinfection responses during high traffic periods when avoiding irradiating vulnerable objects (e.g., people) is important, as well as to reduce energy costs and maximize service life of the light sources. Tunability is generally performed by adjusting the number of light beams recruited to disinfect a specific volume, or by adjusting the intensity, beam shape, or wavelength of light in each beam, or a combination thereof.

The disinfection method may be performed by a human user, by a programmed controller or by a combination of a human user and a programmed controller. In one embodiment, the disinfection system described above is used to perform the method. In another embodiment, a human user localizes the at least one volume in space requiring disinfection, whereas the other method steps are performed by either the human user or the programmed controller. In particular, human control of the system is utilized as a means of acquiring data to optimize algorithms intended to oversee or take over the involvement of a human. Algorithms include semi-quantitative algorithms and for example neural networks which can in part mimic the behavior of a human.

The disinfection system comprises a plurality of disinfecting light sources capable of killing or otherwise rendering harmless infectious organisms or pest organisms that carry infectious organisms. The disinfecting light source preferably produces a beam of disinfecting light. A light beam or beam of light is a directional projection of light energy radiating from the light source. A beam of light provides illumination performance that is better than the inverse square of an incoherent radiating light source. Beams may be produced by a laser, or by directing light using optical elements, such as lenses, mirrors and the like, or by attenuating light in at least one direction and aggregating light in another direction. Preferably, the beam of light has an angle of dispersion of 15° or less.

The light from the light source may be incoherent or coherent light. Coherent light is light in which the phases of all electromagnetic waves at each point on a line normal to the direction of the beam are identical (e.g., laser light). Whether the light is coherent or incoherent, the light source is preferably directed, preferably a beam-producing light source. The beam of light may be produced in a coherent light source, such as a laser. Lasers may be UV lasers, visible light lasers or combinations thereof. A combination of lasers may involve beam mixing or a frequency modification operation, for example. Incoherent light can be formed into a beam by subtracting light from at least one direction of the incoherent light and aggregating light in at least one other direction of the incoherent light. For example, incoherent light can be formed into a bean by focusing, directing and/or collimating light from an incoherent light source. Focusing, directing and/or collimating may be accomplished, for example, with a mirror, a lens (e.g., a condensing lens or Fresnel lens), a system of lenses, a collimator, tube, a channel or any combination thereof. Lenses preferably concentrate shorter wavelengths at the volume in space while maintaining or maximizing the dispersion of longer wavelengths.

Preferably, the light used for disinfection has a wavelength in a range of 180-500 nm, although light with wavelengths outside that range could be used if the power is sufficient for disinfection. In some embodiments, the light source may emit light of a lower frequency. Light having wavelengths in the ultraviolet region is preferred, more preferably light having at least some wavelengths in the UV-C region. Light having wavelengths from 180-280, especially 200-280 nm, is of particular note. Frequency multipliers may be employed to increase the frequency (decrease the wavelength) of the light. Thus, frequency doubling operations may be employed in the system to increase the frequency of the light to an appropriate level for disinfection Frequency multiplying may be accomplished by known techniques, for example by passing the light through various kinds of crystals, and may be performed at arbitrary conversion efficiency to achieve a beam of mixed wavelengths, to increase the service life of optical elements and/or help localize the beam.

The light source for disinfection preferably comprises a plurality of coherent light sources, for example one or a plurality of lasers, more preferably a plurality of ultraviolet (UV) lasers. The plurality of coherent light sources is preferably capable of emitting a coherent beam having a coherent light wavelength in the UV-C range, for example in a range of from 200 nm to 280 nm. Residual light from a pump used in a frequency changing operation may help augment disinfection or help localize the beam. The plurality of coherent light sources should be able to emit coherent light beams of sufficient intensity and power to be able to deliver a disinfecting dose of light in as short a period of time as possible. The coherent light source preferably comprises a laser. Some examples of lasers include a Lucinda™ 200 mW 405 nm purple laser or a TOPTICA™ tunable single-frequency laser system, a CNI UV-F-261, etc. Alternatively or additionally, a beam of light may be created by an incoherent source and lens combination, or mirror and lens combination, to reduce inverse square dispersion. Infectious organisms include, for example, bacteria, viruses and the like. Pest organisms include, for example, insects, mites, arachnids and the like.

The plurality of light sources may comprise a combination of different disinfecting light sources having different wavelength ranges, power outputs, beam geometries or other light source parameters. The light sources are preferably variable in power and/or variable in frequency/wavelength so that the power output and/or frequency/wavelength of a light beam can be adjusted appropriately according to a disinfection task determined by the controller based on the collected data. The light sources are preferably variable in their beam geometry and may be adjusted to create a tight beam of higher intensity light or a more dispersed beam of lower intensity light. Preferably, the light sources kill or otherwise render harmless the infectious organisms themselves.

An advantage of a light beam over lamps lies in the increased ability to selectively disinfect spatial volumes at a faster rate for any given power and electricity consumption rate, reducing the dose of light to volumes of space which do not require disinfection, while being able to minimize irradiating vulnerable objects with incident or reflected beams, thereby simultaneously permitting human activity in high traffic environments while performing disinfection operations rapidly. Even so, the diameter of a light beam may be controlled by collimation or expansion, or the energy of the light beam modulated, to further optimize a particular disinfection task. The extent to which vulnerable objects, such as humans or portions of humans, may be irradiated depends on the wavelength of light and intensity of light employed in the beam. In general, the system minimizes exposure to vulnerable objects.

The disinfecting light sources are mounted at convenient sites and in sufficient numbers in the environment to be protected to offer the ability to disinfect at least most spatial volumes, preferably all spatial volumes, in the environment to be protected. This generally requires more than one vantage point. For example, light sources may be mounted on the ceiling, either alone or in pods, and aligned so that the beam from at least one light source can be incident to any volume at any time in the environment. The light sources may be movably mounted so that the light sources can be rotated or translated if needed in order to successfully target any desired spatial volume at any time in the environment. Further, the system may comprise reflectors (e.g., mirrors), and the environment equipped with the reflectors so that the beam from one or more of the light sources can be redirected to be incident to the spatial volume in the environment or redirected to avoid a target that is not supposed to be hit by the light source's beam. Reflectors may be movably mounted, if desired, to change the angle of incidence and reflection of the light source's beam. One or more of the light sources may comprise components that are separable so that heavier components, for example a pump of a laser, can remain stationary while lighter components, for example frequency multipliers, lenses, mirrors and the like, can be moved to direct the light source's beam.

In addition to the at least one light source, a supplemental disinfection component can be included in the system. For example, the system may further comprise at least one non-coherent ultraviolet light source for disinfection, such as an ultraviolet LED lamp, UV bulb, dispersed laser or the like. The supplemental disinfection component is also controllable by the controller based on the data collected. The supplemental disinfection component would be useful during low- or no-traffic periods for more broad-based disinfection of the environment. The supplemental disinfection component may be affixed to a component that allows translation in space.

The disinfection system comprises one or a plurality of imaging devices capable of collecting data about the environment to be protected. Preferably, the one or a plurality of imaging devices comprises one or more of a 2-D camera, a 3-D camera, a thermal camera, a short wave infra-red (SWIR) camera, a stereo vision camera, a time-of-flight (TOF) sensor or any combination thereof. The one or a plurality of imaging devices preferably comprises a plurality of imaging devices, more preferably a visible light camera and/or an infrared light camera, yet more preferably at least one camera, more preferably at least one visible light camera and at least one infrared light camera. The imaging devices may be movably mounted so that the imaging devices can be rotated or translated if needed in order to successfully scan the desired amount of the environment to be protected. The one or a plurality of imaging devices preferably comprises at least one imaging device that is capable of capturing time series data.

The relationship finder determines relative physical positions of the beam-producing light sources and the at least one imaging device. The relationship finder may comprise a human user or a set of instructions programmed into the programmed controller. The relative physical positions of the beam-producing light sources and the at least one imaging device may be determined by the human user by visual observation. Alternatively, or additionally, the relative physical positions of the beam-producing light sources and the at least one imaging device may be determined from one or more objects detected by the at least one imaging device in the field of view of the at least one imaging device, from electromagnetic radiation (e.g., light) detected by the at least one imaging device in the field of view of the at least one imaging device and sound captured by sound detectors in the environment. Alternatively, or additionally, the relative physical positions of the beam-producing light sources and the at least one imaging device may be determined by wireless localization employing wireless signaling devices on the beam-producing light sources and the at least one imaging device, whereby positions and directions of the beam-producing light sources and the at least one imaging device are automatically determined in a region of space by the controller.

The physical positions of the beam-producing light sources are used to determine geometric relationship between at least one of the beam-producing light sources and the volume in space. Determining the geometric relationship preferably comprises calculating distance and/or direction of the beam-producing light sources to the volume in space to be disinfected. In some embodiments, because the relative positions of the beam-producing light sources with respect to each other can be determined from the relative physical positions of the beam-producing light sources and the at least one imaging device, the physical position of one of the beam-producing light sources may be used to calculate distance and/or direction of one or more of others of the beam-producing light sources to the volume in space. In some situations, only one imaging device is correctly situated to observe a volume in space in need of disinfection. In such an eventuality, the ability to calculate the location of the volume in space relative to each of the beam-producing light sources that may be available to project beams of light to that volume in space profits from the ability to calculate distance and/or direction of one or more other beam-producing light sources to the volume in space based on the physical position of only one of the beam-producing light sources. An available light source is a light source that has direct or indirect line of sight to the volume in space.

The disinfection system comprises a programmed controller for controlling the plurality of light sources based on the data collected from the one or plurality of imaging devices and from known positions and dispersion geometries of the beam-producing light sources. The programmed controller is programmed with control software, preferably a neural network that synthesizes the collected data. The controller performs the method and is operatively linked to, for example in electronic communication with, the one or plurality of imaging devices and/or to the plurality of light sources. Electronic communication may be provided through wires or wirelessly. The controller may comprise, for example, a computer, an output device and an input device, the computer comprising a microprocessor for controlling operations and a non-transient electronic storage medium for storing the collected data and/or for storing computer executable code for carrying out instructions for implementing the method. The computer may further comprise a transient memory (e.g., random access memory (RAM)) accessible to the microprocessor while executing the code. A plurality of computer-based apparatuses may be connected to one another over a computer network system and geographically distributed. One or more of the computer-based apparatuses in the computer network system may comprise a microprocessor for controlling operations and a non-transient electronic storage medium for storing the collected data and/or for storing computer executable code for carrying out instructions for implementing the method, and the computer-based apparatuses in the network may interact so that the disinfecting operation may be carried out automatically from remote locations. The output device may be a monitor, a printer, a device that interfaces with a remote output device or the like. The input device may be a keyboard, a mouse, a microphone, a device that interfaces with a remote input device or the like. With a computer, data (e.g., images from the imaging devices) may be a graphically displayed in the output device. There is also provided a computer readable non-transient storage medium having computer readable code stored thereon for executing computer executable instructions for carrying out the method.

In some embodiments, the disinfection system may be partially or completely wearable or carriable by a person. The wearable or carriable disinfection system may be trained to disinfect a spatial volume, for example the volume directly in front of the person's face. The light sources, the at least one imaging device and/or the controller may be worn or carried as part of a phone, pin, bracelet, wristband, headband, a clip clipped on to a shirt, or the like. In some embodiments, the disinfection system may be affixed to a vehicle.

Localization of the volume in space involves determining boundaries or a probability distribution in 3-dimensional space within which potentially exists an infectious organism or a pest organism and within which a disinfection operation is to be performed. The plurality of beam-producing light sources can then be utilized to disinfect the volume in space. Preferably, stereo images produced from the collected image data are used to localize the volume in space requiring disinfection. In some embodiments, localization is accomplished from one or more of detection of objects, detection of orientation of objects, detection of orientation of objects, detection of motions of objects, and detection of interaction between objects in the field of view of the at least one imaging device.

The controller or a human operator may further classify objects by object types. In order for the controller to classify the objects, the control software may have a classifier programmed therein that analyzes images collected by the imaging devices and classifies objects in the images after having previously been trained from a pre-programmed dataset of object types to determine the type of object, and then based on the type, determines whether the object is or is not a potential source of infection. The controller may further rank each object according to the risk that the object harbors an infection. The dataset of object types comprises a listing of different objects that may be encountered in the environment to be protected together with the objects' image characteristics and a risk ranking for harboring an infection. A controller programmed with a neural network is particularly useful in that the controller can be readily trained to recognize and discriminate different objects.

An object is anything that has a surface. Objects may be, for example, humans, portions of humans (e.g., human faces), keypads (e.g., in elevators, banks, stores and the like), handles (e.g., door handles, faucet handles, toilet handles, appliance handles and the like), walls, floors, ceilings, doors, windows, light fixtures, furniture, (e.g., tables, chairs, couches), telephones, computers, toys, clothing (e.g., gloves, caps, hats, shoes), tools, instruments, cell phones, organisms, water droplets suspended in air, portions of the aforementioned objects, and the like. As indicated above, one object may be part of another object. For example, a person is an object and a hand of a person is another object. Some of the objects most likely to be classified as potential sources of infection include, for example, organisms (e.g., pest organisms, humans, pet animals, body parts of humans and pet animals (e.g., a finger, hand, face and foot, which may or may not be clothed)), water droplets suspended in air (e.g., due to speaking, sneezing, coughing, yawning, spitting, hyperventilating or other similar dispersion events), and the like.

The objects may be further classified to include vulnerable objects, which is a set of defined objects to avoid harmfully irradiating with the light source. Vulnerable objects include and encompass specific organisms (e.g., a person, in particular a child) and portions of organisms (e.g., a portion of a person) to avoid harmfully irradiating. The controller is preferably further programmed to control the light sources to minimize irradiating a vulnerable object, or in some cases to altogether avoid harmfully irradiating vulnerable objects. The controller may wait for a vulnerable object to move or switch off or redirect one or more of the light sources to avoid harmfully irradiating the vulnerable object, while simultaneously recruiting one or more alternate light sources to take over or continue disinfection, if desired. Vulnerable objects preferably comprise humans, pet animals and specific portions thereof including eyes and exposed skin. In this regard, it is especially useful for the controller to be able to recognize and discriminate high-risk features (e.g., eyes, face, uncovered skin, child, pregnant person) of vulnerable objects that should not be irradiated so that the controller can control the light sources to avoid hitting those features, while still being able to discriminate worn clothing (e.g. gloves, caps, and the like) so that the controller can control the light sources to disinfect the worn clothing, if desired.

Disinfection of volumes in space is an objective the system and method. To determine spatial volumes that need to be disinfected, the system is preferably trained to detect motions of objects in the field of view of the at least one imaging device. The motion may be a translation of an entire object through space or a motion of a portion of the object relative to other portions of the object. The system is preferably also trained to analyze a direction, and preferably also speed of the object moving through space. In addition, the system is preferably trained to determine a motion type, for example translation of an entire object through space or a motion of a portion of the object relative to other portions of the object. Examples of motions of an entire object include, for example, a person walking, a door opening or closing, a window opening or closing, a chair having its location changed, etc. Examples of motions of portions of an object relative to other portions of the object include, for example, head movements (e.g., head turns, nods, etc.) relative to a person's body, hand motions relative to a person's body, arm motions relative to a person's body, turning or bending of a person's torso relative to the person's body, turning of a door know, a switch being flipped, etc. Motions are preferably categorized into those that are unlikely to cause infection and potential infection-causing motions. Potential infection-causing motions comprise, for example, speaking, a yawn, a cough, a sneeze, a spit, hyperventilation, increased respiratory rate or a deep exhalation.

Water droplets, having one or more infective organisms suspended therein, dispersed into the environment from a person's face are a primary source of infection, however identifying location of water droplets suspended in air is difficult, especially when the droplets are very small. In the present system and method, the location of such water droplets can be correlated to the detection of potential infection-causing motions that produce such droplets (e.g., normal breathing, speaking, yawning, coughing, sneezing, spitting hyperventilating, increase of respiratory rate or deeply exhaling). The controller is preferably programmed for facial recognition and facial orientation. The volume in space to be disinfected may be localized from position of the face and/or a direction in which the face is pointing. The volume in space to be disinfected may further be localized from translational or non-translational motion of the face, or changes in facial features identified as the potential infection-causing motion. The controller may be programmed to calculate a dispersion pattern of potentially infective organisms in front of the face based on position and orientation of the face, and may be further modified by motion of the face such as heavy breathing, coughing, sneezing, yawning and the like. Known dispersion tendencies of potentially infective organisms may also be factored into the calculation of the dispersion pattern, whereby the potentially infective organisms are classified based on their dispersion tendencies and the controller utilizes the classification dispersion tendencies when calculating the dispersion pattern. The dispersion pattern may include dispersion of the potentially infective organisms onto surfaces of other objects proximate to the face. The diffusion pattern is calculated based on the strength of the potential infection-causing motion, including propulsion in breath, diffusion characteristics of water droplets, and air movement patterns (convection and bulk flow) in the environment. Calculation of dispersion pattern may be accomplished via software such as a physics engine. The dispersion pattern includes surfaces upon which infectious elements may have been deposited.

In some embodiments, the controller may be programmed to disinfect the localized volume in space after an object has moved away from the volume in space. Such a delay in disinfection is particularly useful when the object is a vulnerable object to the particular light used for disinfection, and in some cases whose presence may have been responsible for the need to disinfect the volume in space. Thus, the motion of the entire object may be tracked by the system, and once the object has moved a safe distance away from the localized volume in space, the system is operated to disinfect the localized volume in space. Stereoscopic vision, facilitated by using a plurality of imaging devices to collect image data, is particularly useful for tracking the position of moving objects in three dimensions.

In some embodiments, the controller may be programmed to disinfect the localized volume in space while an object is still within or adjacent to the space.

The controller may utilize detection of interactions between objects (e.g., touching, conversations, or the like) in the field of view of the at least one imaging device to localize the volume in space to be disinfected. To utilize detection of interactions between objects, the controller is trained to recognize interaction types. Touching may comprise a casual or a deliberate contact between a potential source of infection and another object. The volume in space in which the objects touched is localized including a potential dispersion pattern for an infection, and the localized volume disinfected after any vulnerable objects have moved away. Non-touching interactions, such as conversations between people, may create spatial volumes between people that contain infections. The controller utilizes the orientation and separation of the faces of the people in the conversation to localize a volume in space to be disinfected. Further, in the case of conversation or other breath exhalation, dispersion patterns may result in sub-localization of an aggregate region between the two faces warranting priority for disinfection. The controller may conduct the disinfection operation after or during the conversation. The volume in space requiring disinfection may include portions of the heads or faces if so required.

The controller is also programmed to calculate the direction to the volume in space for each available beam-producing light source. Preferably, the controller calculates distance from and a connecting vector to the volume in space (i.e., distance and direction). Once the volume in space is localized, the location and extent of the localized volume in space and the known positions of the beam-producing light sources can be used to make the distance and/or vector calculations. The distance and/or vector calculation for each available beam-producing light source can be made separately for sub-regions in the volume in space. Each distance and/or vector calculation preferably accounts for the diameter of the beam from the beam-producing light source and the known dispersion geometry of the beam-producing light source. Distance and vector calculations for each available beam-producing light source informs the controller on how to control (e.g., how to change the direction of) each beam-producing light source during a disinfection operation in order to ensure sufficient coverage of the volume in space during the disinfection operation. Calculation of the vector also permits the controller to determine whether there are any intervening vulnerable objects in the field of view of the at least one image device along either an incident vector or a reflected vector of the beam, which allows the controller to control the light sources to avoid harmfully irradiating the vulnerable objects. Any one or more of a variety of other techniques can be used to calculate reflection vectors, for example techniques utilizing time of flight systems (e.g. radar, sonar), parallax effect (e.g. stereoscopy) or laser proximity sensors may be used to define distance or spatial position between the light sources and the objects in the environment, including specific sites of interest, as well as adjacent or nearby sites, so as to define planes of surfaces of the objects in order to calculate reflection angles of incident light, such that the reflection vectors may be accounted for in any given disinfection task. Thus, prior to undertaking a disinfection operation while in active mode, the system uses any combination of object classification, comparison of objects' pixel data (e.g., color) to a database, distance data to objects, object size, thermal and other spectroscopic characteristics of objects and reflection vectors to calculate probability of hitting a target volume in space and not a vulnerable object.

The controller is programmed to coordinate light beams projected from each of the available beam-producing light sources to the volume in space requiring disinfection to reduce or maintain time required to deliver a threshold disinfecting light dose to the volume in space requiring disinfection. Preferably, the controller coordinates the light beams to disinfect the volume while minimizing disinfection time, reducing energy consumption, maximizing bulb life of the beam-producing light sources, avoiding interaction of the light beams or any combination thereof, whether incident or reflected, with a detected vulnerable object. Further, if the volume requiring disinfection contains also contains an object to be disinfected, the controller preferably coordinates the light beams to also disinfect a surface of the object to be disinfected. How the controller coordinates the light beans depends on a number of factors including one or more of the number of beam-producing light sources available to disinfect the volume in space, the power of the available beam-producing light sources, the distances of the available beam-producing light sources to the volume in space, available modifications to the geometry of the beam, the wavelengths of available light and their potential harm, and the size of the volume in space and the available time within which the disinfection operation must be completed. The light beams from the beam-producing light sources are coordinated to sweep through the volume in space for an amount of time to deliver at least a threshold energy density in the entire volume sufficient to disinfect the volume in space. In some cases, such as where two or more people are close together, it may be impossible to perform the disinfection of the volume in space adjacent to the faces of the persons without irradiating the faces. In these cases, the controller may minimize irradiation of the face and particularly to exposed skin of the persons, and/or preferentially use shorter wavelength UVC light.

Further, in some embodiments, data may be reviewed by a human operator to either actively or passively approve targeting of a volume in space to be disinfected. Review may be performed, for example, by an on-site safety officer, and in some situations with such human over-sight, it may be possible to utilize higher energy light sources for disinfection than could be used without the presence of human over-sight. From a regulatory perspective, human over-sight permits overriding the automated controller thereby providing an extra layer of safety. The ability to provide human over-sight in the system is also very useful during the training phase of the programmed controller and during initial calibration of the disinfection system in a particular environment.

Image data, disinfection data and data generated from calculations performed by the controller may be recorded and stored in long-term computer readable non-transient memory as a historical record that can be accessed and reviewed at a later date. The historical record is useful for providing retrospective evidence that disinfection operations did not harmfully irradiate a vulnerable object that should not have been irradiated, and to provide evidence that the system is complying with relevant regulatory requirements.

The controller may be further programmed to rank localized volumes in space according to the risk that each spatial volume harbors an infection. The ranking is preferably based on the type of objects that have been in the spatial volume. The dataset of object types comprises a listing of different objects that may be encountered in the environment together with the objects' image characteristics and a risk ranking for harboring an infection. The controller can then prioritize the spatial volumes having a higher risk ranking, and coordinate the light sources to disinfect high risk volumes first.

In some embodiments, the system further comprises a projector controlled by the controller, the projector capable of projecting messages on to surfaces of objects. The controller may be programmed to identify whether a person is oriented towards an object that has been disinfected, and then control the projector to project a message onto a surface of the disinfected object or on to a surface of another object adjacent to the disinfected object to indicate that disinfection has been performed.

With reference to FIG. 1, one embodiment of a laser-based disinfection system 1 comprises a plurality of ultraviolet (UV) lasers 3 mounted on first rotary motors 4 and a plurality of wide field of view multispectral cameras 5 having infrared (IR), visible, UV spectrum sensitivity mounted on second rotary motors 6. Each of the lasers 3 are equipped with wireless radio transmitters 8*a*, while each of the multispectral cameras 5 are equipped with wireless radio transmitters 8*b*. The lasers 3 are capable of emitting coherent ultraviolet light, and can also emit coherent light in the visible spectrum, or in some set of specific wavelengths.

The lasers 3, first rotary motors 4, cameras 5, second rotary motors 6 and the wireless transmitters 8*a*, 8*b* are in electronic communication with a controller comprised in a computer system 10. The computer system 10 comprises a central processing unit (CPU) 12, an input/output (I/O) component 14, a wireless radio receiver 8*c* and a non-transient computer memory 16. The computer memory 16 contains a computer program 18, calibration data 20 and collected data 22. The computer program 18 comprises a deep neural network 19 based on a mathematical optimization model developed to make decisions based on a synthesis of the collected data 22 and the calibration data 20 in order to properly operate the disinfection system 1. The calibration data 20 comprises pre-loaded common information about the system 1 and pre-acquired information about the characteristics of objects likely to be encountered in the environment to be protected by the disinfection system 1. The collected data 22 comprises image data collected by the cameras 4 and position data for the lasers 3 and cameras 5 acquired from the wireless radio transmitters 8*a* and 8*b*, respectively, all of which is collected during real-time operation of the system 1, and which is stored in the computer memory 16. The deep neural network is pre-trained so that the calibration data 20 contains information about the potential sources of infection and other objects that will likely be encountered, and is capable of learning from the collected data 22 to be able to revise the calibration data 20 during system operation.

The central processing unit (CPU) 12 receives image data from the cameras 5 and position data collected from the wireless radio transmitters 8*a*, 8*b*, as well as positional data from rotary encoders on the rotary motors 4, 6, and executes decisions made by the computer program 18 by transmitting data to independently control the rotary motors 4, 6 independently change the orientation of the lasers 3 and cameras 5, respectively, and independently switch the lasers 3 on/off, adjust the power output of the lasers 3 and/or adjust the frequency of the lasers 3. Data is received by and transmitted from the computer system 10 wirelessly, although a hard-wired system could be employed of the computer system 10 is sufficiently close to the lasers 3 and cameras 5. The computer program 18 programmed into the computer system 10 synthesizes the image data collected from the cameras 5 to classify the objects in the field of view of the cameras 5 according to risk of harboring an infection on the basis of the calibration data 20 about the objects likely to be encountered in the environment. The computer program 18 further localizes at least one volume in space requiring disinfection in the field of view of the cameras 5 by analyzing the objects in the field of view, the motions of objects in the field of view and interactions between the objects in the field of view. Having localized the volume(s) in space requiring disinfection, the computer program 18 calculates distance from and connecting vector to the volume(s) in space for each laser of the plurality of lasers 3 to determine which of the lasers 3 can be utilized to disinfect each of the volume(s) in space in need of disinfection. Based on the classification of the objects, the localization of the volume(s) in space and the positions of the lasers 3, the lasers 3 are coordinated to project laser beams from each of the available lasers 3 to the volume(s) requiring disinfection. The laser beams are coordinated to minimize the time required to deliver a threshold disinfecting light dose to the volume(s) in space requiring disinfection. The lasers 3 are controlled independently so that the coordination plan can be changed in real time to accommodate vulnerable objects (e.g., people) that may intersect with a laser beam during the disinfecting operation. The lasers 3 are also coordinated to minimize disinfection time, maximize bulb life of the lasers 3 and avoid interaction of the laser beams, whether incident or reflected, with a detected vulnerable object.

Figure 2:
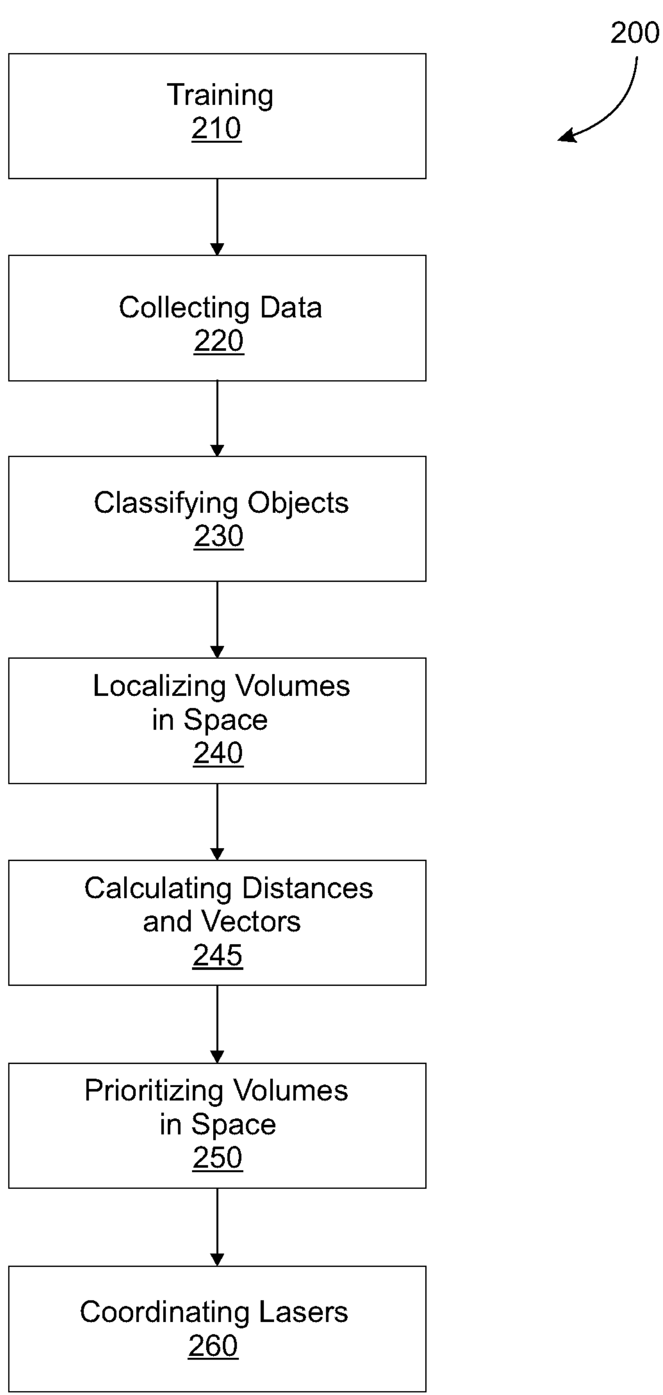
FIG. 2 depicts a flowchart illustrating a method of disinfection using the laser-based disinfection system of FIG. 1.

With reference to FIG. 2, a method 200 of disinfecting using the laser-based disinfection system 1 is depicted. The method comprises:

Training 210. Calibration data related to components of the disinfection system are stored in the computer memory, including data about the rotary motors, the lasers, the cameras and the wireless radio transmitters associated with the lasers and cameras. The data related to the components of the disinfection subsystem include, for example, the absolute and relative positions and orientations of the components in the environment. The deep neural network of the computer program is further trained: to recognize object types (i.e., objects that are potential sources of infection, vulnerable objects, objects that are not potential sources of infection, parts of the objects that are potential sources of infection and parts of the objects that are not potential sources of infection) in the environment; to recognize movement of objects and parts of the objects, (i.e., whether the object or parts of the object are moving or not moving); and, to calculate trajectories of moving objects and object parts within the environment. Training the system to recognize faces and orientation of the faces, together with potential infection-causing motions is particularly useful. The object types are stored in the computer memory as part of the calibration data. Object properties are stored in the computer memory and assigned to each object type, the object properties including, for example, whether the object is a vulnerable object not to be harmfully irradiated, whether the object is or is not a potential source of infection, whether the object commonly interacts with a potential source of infection, whether the object is a stationary or mobile object, likely surface material of the object, UV reflectivity of the surface material, transparency of the material, angles and paths of laser beam reflection from the object relative to the possible orientations of the lasers, and the like. In some instances, the object properties assigned to the object types may adjusted based on the particularities of the environment when the disinfection system is being installed in the environment. Each object property is assigned a weighting factor indicating the extent to which the object property contributes to a risk that the object type harbors an infection. The sum of the weighting factors provides a measure of the risk that the object type harbors an infection.

Collecting data 220. Data about the environment to be protected is collected in real time and stored in the computer memory as collected data. The cameras collect image data within their respective fields of view, and the wireless radio transmitters associated with the cameras and lasers transmits position data of the cameras and the lasers to the computer to be stored in the computer memory. The collected image data are assigned a collection time so that the image data and position data are time sequenced to permit the deep neural network to recognize movement of objects and calculate trajectories of moving objects.

Classifying objects 230. The neural network compares the collected image data to the stored calibration data to classify the objects in the fields of view of the cameras into object types with corresponding object properties for the object types. The neural network calculates and assigns a risk of harboring an infection to each object in the fields of view of the cameras based on the measure of risk in the calibration data for the corresponding object type. The neural network also uses the time sequenced data to classify each object as moving or not moving. The neural network also uses the time sequenced data to determine and classify interactions between objects.

Localizing volumes in space 240. Based on the classification of the objects, the motions of the objects and the interactions between objects the neural network generates a risk map, which is a discretized representation of the spatial volume of the environment showing spatial volumes potentially containing a source of infection. In some examples each camera will have its own map where individual pixels are registered to those of all other maps at calibration. In some examples a common model will be created by data derived from the plurality of cameras. Spatial volumes potentially containing a source of infection may include spatial volumes in which an object that is a potential source infection exists, such as those containing a person or portion of a person such as a head or face, spatial volumes through which an object that is a potential source infection has moved including where appropriate allowances for dispersion which may be calculated with for example a physics engine, spatial volumes toward which an object that is a potential source infection is moving, spatial volumes in which an object that is a potential source infection interacts with another object, and spatial volumes adjacent to an object which is a source of infection including for example a face and where the volume is defined based on the orientation of the face. Localization involves delineating the boundaries in space that potentially contain a source of infection. Determining the extent of the boundaries is derived from a number of factors including the size of the object that is a potential source, the extent of movement of the object, whether there is a potential infection-causing motion, the nature of any potential infection-causing motion (e.g. breathing, heavy breathing, speaking, coughing, sneezing, yawning and the like) including known dispersal patterns therefor, air flow parameters in the environment, the existence of other objects proximate the potential source of infection, among others.

Calculating distances from and vectors to the volumes in space 245. Calculation of the distance from and the vector to the volume in space to be disinfected for any given laser is determined from the position of the laser as provided by the wireless radio transmitter and the image data collected by the cameras. The volume in space must be imaged by at least one of the cameras, and the image data used to calculate distance and vector for at least one of the lasers. If a plurality of cameras is able to image the volume in space, calculation of the distances and vectors for more of the lasers is simplified. However, because the positions of the lasers relative to each is known from the wireless radio transmitters, it is possible to calculate distances and vectors for all of the lasers from the distance and vector for only one of the lasers. Calculation of distances and vectors for each laser to the volume in space provides an indication of which lasers are available to disinfect the volume in space. Some lasers may be located in a position where it is impossible for a beam from that laser to reach the volume to be disinfected.

Prioritizing volumes in space 250. Once the volumes in space have been localized, the volumes in space are prioritized as to which ones should be disinfected first. The neural network prioritizes volumes in space at least partially based on movement events, that is relative movements between the potential sources of infection and the other objects, and on assigned risk of harboring an infection. For example, a ranking of disinfection priority is assigned to a volume in space based on the sum of a weighting of: the number of moving objects around and in the volume in pace; the proximity of potential sources of infection to another object; directions in which the potential sources of infection are moving relative to the other objects; whether any potential infection-causing motions has occurred (e.g., a sneeze, a yawn or the like); and, the risks of harboring an infection assigned to the other objects. Higher traffic locations in the environment are given higher priority, i.e., if the number of moving objects around or in the volume in space is higher, the priority ranking is raised for the volume in space. When a potential infection-causing motion occurs in the volume in space, the volume in space is given a higher priority. When the potential sources of infection are interacting with another object, the priority ranking of the volume in space between the objects is raised. When a potential source of infection is moving toward another object, the priority ranking for the volume in space between the objects is raised. If the volume in space contains a vulnerable object the priority ranking of the volume in space is lowered or dropped to zero, until the vulnerable object moves out of the volume in space, in which case the priority ranking is raised.

Coordinating lasers to disinfect volumes in space 260. Once the priority ranking of the volumes in space has been established, the computer system controls the lasers to coordinate laser beams to disinfect the volumes in space in order from highest to lower priority. Because the system is working in real time, the priority rankings may change dynamically, however, the neural network may be trained to complete an existing disinfection task before handling a new higher priority task, unless the assigned priority ranking of the new task exceeds an emergency threshold. The neural network calculates appropriate laser beam parameters (e.g., beam energy, beam frequency, beam orientation) required for a disinfection task based on the size and location of the volume in space to be disinfected and on the known beam dispersion properties of the laser beams. The laser beams are appropriately collimated or expanded, to provide a sufficient quantity of energy over a sufficient period of time in the volume in space. The laser beams are scanned through the volume in a pattern that the controller calculates to minimize disinfection time, maximize bulb life of the lasers and avoids interaction of the laser beams, whether incident or reflected, with a detected vulnerable object. One or more of the laser beams may also be directed to a discrete area on a surface of an object in the volume in space, which may be harboring an infection. In assigning a laser or lasers for a disinfection task, the computer system calculates incident and reflected beam vectors in order to determine which laser or lasers are best suited for the task. Lasers whose beam vectors would could result in harmfully irradiating a vulnerable object (e.g., humans and pet animals) would not be used or would be intermittently switched on and off. In the event that a laser beam needs to be switched off during a disinfection task because a vulnerable object crosses the beam vector, the laser would be turned off for a sufficient time and the disinfection task recalculated or a different laser reassigned to complete the task.

Figure 3:
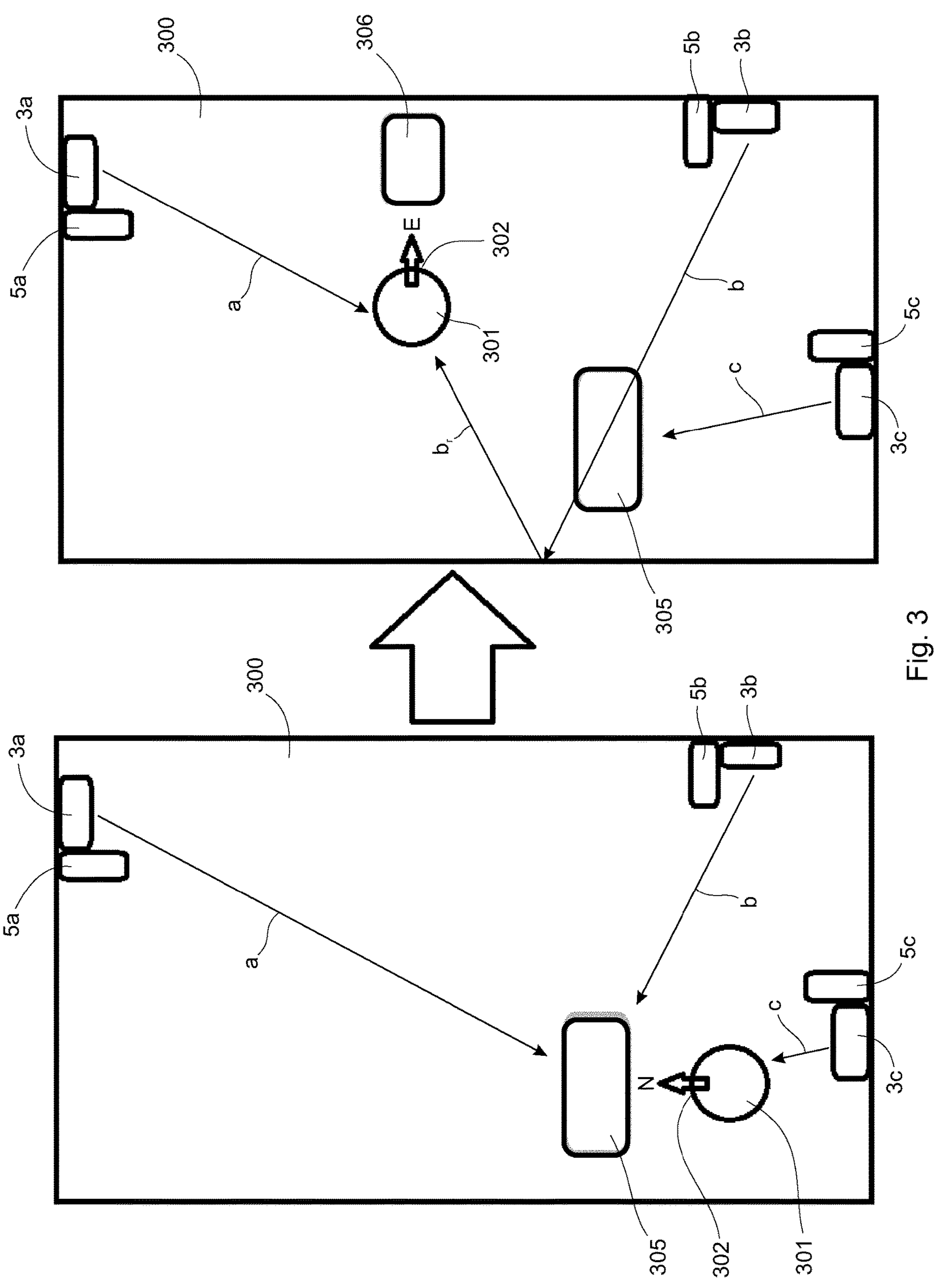
FIG. 3 depicts a schematic diagram of the laser-based disinfection system of FIG. 1 deployed in a room at time step 1 (left) and time step 2 (right) later than time step 1.

With reference to FIG. 3, the laser-based disinfection system of FIG. 1 is depicted deployed in a room 300 at time step 1 (left panel) and at time step 2 (right panel), time step 2 being at a later than time step 1. The room 300 is equipped with three disinfecting lasers 3*a*, 3*b* and 3*c* and three cameras 5*a*, 5*b* and 5*c* colocalized in the room 300 with the three lasers 3*a*, 3*b* and 3*c*, respectively. A computer system (not shown), having a controller and a wireless radio receiver, is in wireless electronic communication with each of the lasers 3*a*, 3*b* and 3*c* and each of the cameras 5*a*, 5*b* and 5*c*. A person 301 is walking in the room 300.

At time step 1 (left panel), a face 302 of the person 301 is visible in the field of view of the camera 5*a*, partially visible in the field of view of the camera 5*b* and not visible in the field of view of the camera 5*c*. The person's face 302 is looking in a direction N. When the person 301 coughs, thereby causing a characteristic motion of the face 302, the cameras 5*a* and 5*b* able to capture images of the face 302 and the region directly in front of the person 301. From the images, the controller is able to recognize that the person has coughed, which is a potential infection causing event, and the images are used by the controller to localize a first volume 305 in space to disinfect based on calibration data about the dispersion characteristics of a cough. The first volume 305 is localized relative to each of the light-sources 3*a*, 3*b* and 3*c* and each of the cameras 5*a*, 5*b* and 5*c*. Incident vectors a, b and c and distances from the lasers 3*a*, 3*b* and 3*c*, respectively, to the first volume 305 are calculated by the controller. At time step 1, the lasers 3*a* and 3*c* cannot be used to disinfect the first volume 305 because the person 301 (i.e., a vulnerable object) is in the paths of the beams from the lasers 3*a* and 3*c*. However, the laser 3*b* can be used to disinfect the first volume 305 at time step 1 because the vector b does not cross the location of the person 301.

In time step 2 (right panel), the person 301 has moved to a different location in the room 300 and is looking in direction E. Now, the first volume 305 cannot be accessed by laser 3*a* due to the person 301 being in the vector a, and also cannot be disinfected by laser 3*b* because a reflection vector br of the vector b from the laser 3*b* off a wall of the room 300 would hit the person 301. However, the first volume 305 can be disinfected by the laser 3*c* because neither incident or reflected light from the laser 3*c* create a safety risk for the person 301. In addition, another cough by the person 301 in time step 2 can be imaged by the three cameras 5*a*, 5*b* and 5*c*, and based on the image data a second volume 306 in space is localized by the controller for disinfection. The second volume 306 is accessible by both the lasers 3*a* and 3*c*, but the laser 3*b* is potentially not available because the laser 3*b* is obstructed by the camera 5*b*. The controller therefore coordinates the lasers 3*a*, 3*b* and 3*c* such that the laser 3*a* is redirected to disinfect the second volume 306, the laser 3*c* is directed to disinfect the first volume 305, and the laser 3*b* is not used. The system disinfects the second volume 306 preferentially by using the laser 3*a* and disinfects the first volume 305 preferentially by using the laser 3*c* because the closer proximity of these lasers to these volumes and known beam divergence properties of the lasers result in a faster disinfection at lower overall energy consumption, thereby maximizing bulb life across the three lasers 3*a*, 3*b* and 3*c*.

Figure 4:
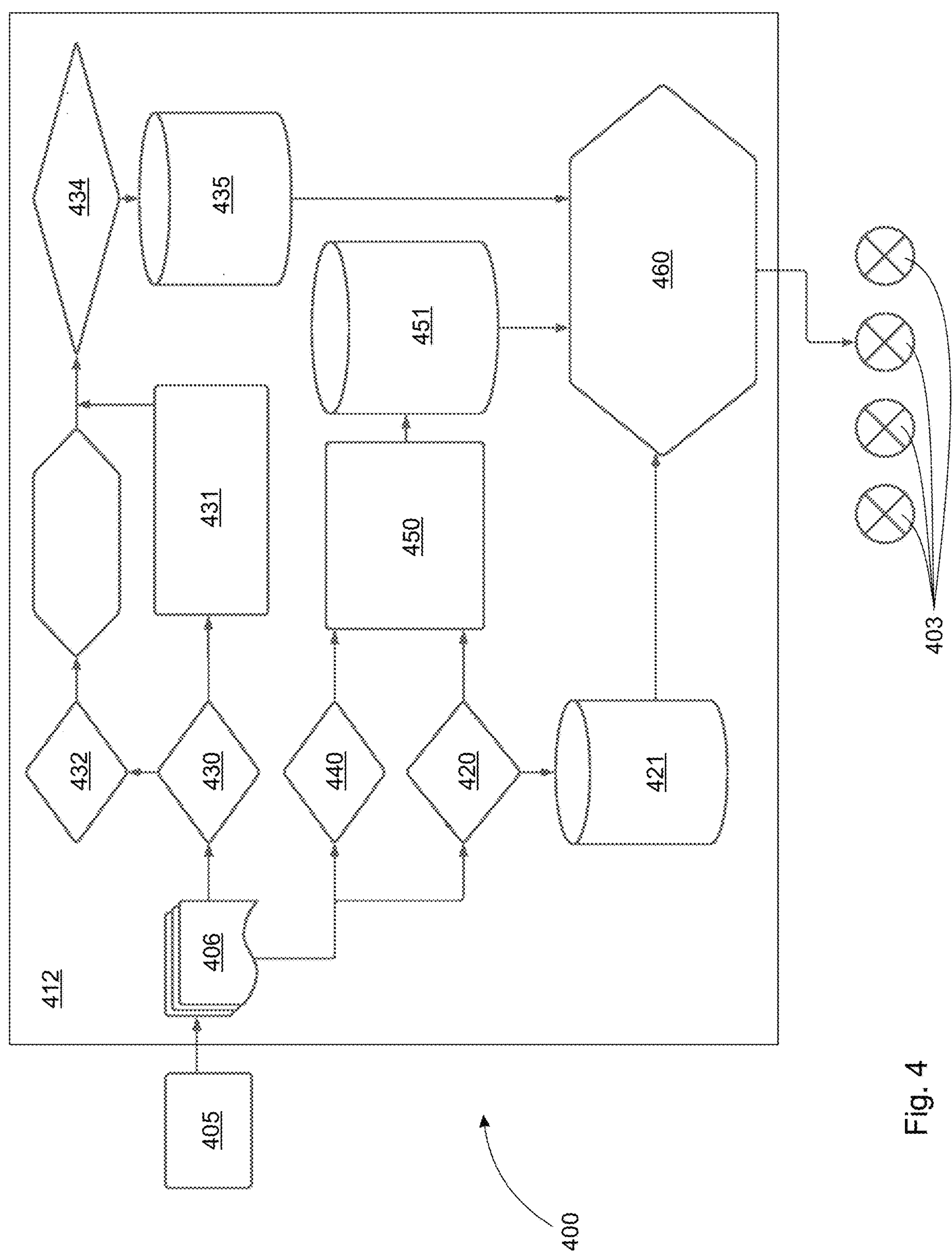
FIG. 4 depicts a schematic diagram illustrating another embodiment of a disinfection system for disinfecting volumes in space and a control method for controlling the disinfection system.

In another embodiment, FIG. 4 depicts a disinfection system 400 for disinfecting volumes in space and a control method for controlling the disinfection system 400. The disinfection system 400 comprises a computer system 412 having computer memory and a programmed controller for controlling the system 400, a plurality of aimable ultraviolet (UV) lasers 403 for disinfection, and a stereo camera 405 that acquires a time series of stereo images 406, the stereo images 406 being stored in the computer memory as collected image data. The controller is in electronic communication with the UV lasers 403, the camera 405 and other components of the system 400.

The computer system 412 has a plurality of modules programmed therein for analyzing the stereo images 406 acquired in time series by the stereo camera 405 and then making decisions on how to control the lasers 403 based on the analysis. The program modules comprise a person detection module 420, an object detection module 440 and a face detection module 430.

The person detection module 420 compares calibration data stored in the computer memory to the image data collected by the camera 405 to first recognize whether an object in the collected image data is a person. The image data associated with an object identified as a person is skeletonized to produce a light skeleton, and the skeleton provides a bounded region in space whose movement through space can be tracked through the time series of stereo images 406. Skeletonization facilitates quick and accurate image processing on the light skeleton instead of an otherwise large and memory-intensive operation on the original image. The skeletonized images over time through a time line set out in the time series of stereo images 406 are stored in skeleton files 421.

The object detection module 440 compares calibration data stored in the computer memory to the image data collected by the camera 405 to recognize objects in the collected image data other than the people detected by the detection module 420. Such objects are usually static, therefore skeletonization is not needed because the objects do not move in space through the time series of stereo images 406 collected by the camera 405. The objects do have surfaces, though, which can interact with the person moving through space.

An interactions sub-module 450 analyzes the time series of stereo images 406 to determine whether there was any interaction between the persons detected by the person detection module 420 and objects detected by the object detection module 440. Where an interaction has occurred (e.g., a surface of an object touched by a person), the locations of those interactions on the surfaces of the objects are stored in interactions files 451.

The face detection module 430 compares calibration data stored in the computer memory to the image data collected by the camera 405 to recognize whether an object in the collected image data is a person's face. Once an object in the collected image data is identified as a person's face, a face orientation sub-module 431 identifies the orientation of the face of a person relative to the rest of the environment over time through a time line set out in the time series of stereo images 406. Also, a face action sub-module 432 identifies over time through the time line set out in the time series of stereo images 406 whether the face underwent a potential infection-causing motion. If the face action sub-module 432 identifies a potential infection-causing motion, the face action sub-module 432 identifies the type of motion (e.g., cough, sneeze, yawn, etc.) and associates the potential infection-causing motion with the time line set out in the time series of stereo images 406. Based on the face orientation data and the face action data, which includes information about dispersion patterns resulting from the type of infection-causing motion, a spatial volume localizing sub-module 434 calculates a volume in space to be disinfected, and stores the localized volume in volumes files 435 for each time in the time line set out in the time series of stereo images 406.

Data about the skeletonized images, the object interactions and the volumes in space are synthesized by a scheduler 460 to prioritize disinfection operations. Localized spatial volumes in front of a person's face, including objects in the localized spatial volume during a potential infection-causing motion, are given higher priority than spatial volumes that were occupied by a person. Spatial volumes that were occupied by a person are given higher priority than surfaces of objects that interacted with the person. Based on the prioritization, the controller operates the plurality of lasers 403 to undertake disinfection operations. Where multiple disinfection operations must be performed simultaneously, the controller can coordinate the plurality of lasers 403 to undertake simultaneous disinfection operations of multiple volumes in space, having regard to the positions of the lasers 403 to the volumes to be disinfected and to the positions of vulnerable objects (e.g., persons) relative to the lasers 403. Factors that could influence prioritization include the availability of the plurality of lasers 403 at any given time to undertake the disinfection, the current positions of any vulnerable objects (e.g., persons) in relation to the plurality of lasers 403, distances from the lasers 403 to the volumes to be disinfected, etc.

The novel features will become apparent to those of skill in the art upon examination of the description. It should be understood, however, that the scope of the claims should not be limited by the embodiments, but should be given the broadest interpretation consistent with the wording of the claims and the specification as a whole.

The invention claimed is:

1. A disinfection system comprising:

a plurality of beam-producing light sources for disinfection;

at least one imaging device for collecting image data in a field of view of the at least one imaging device;

a relationship finder to determine relative physical positions of the beam-producing light sources and the at least one imaging device; and, a programmed controller for controlling the beam-producing light sources based on the image data collected from the at least one imaging device and from known positions and dispersion geometries of the beam-producing light sources, wherein the controller is programmed to:

localize at least one volume in space requiring disinfection;

calculate direction to the at least one volume in space for each available beam-producing light source; and, coordinate at least one light beam projected from the available beam-producing light sources to the at least one volume requiring disinfection to reduce or maintain time required to deliver a threshold disinfecting light dose to the at least one volume in space requiring disinfection, wherein the controller calculates distance from each available beam-producing light source to the at least one volume requiring disinfection and, combined with dispersion properties of the light beams, coordinates the light beams to disinfect the at least one volume in space while reducing or maintaining disinfection time, reducing energy consumption and maximizing bulb life of the beam-producing light sources, wherein the volumes in space are prioritized as to which ones should be disinfected first and prioritization of the volumes is changed dynamically as new data is acquired in real time, and the controller is programmed to complete an existing disinfection before a new higher priority disinfection unless an assigned priority ranking of the new disinfection exceeds an emergency threshold.

2. The system of claim 1, wherein the at least one volume requiring disinfection comprises a plurality of volumes requiring disinfection, and the controller coordinates the available beam-producing light sources to disinfect the plurality of volumes while maximizing disinfection efficiency, minimizing time to disinfection, maximizing bulb life of the beam-producing light sources and minimizing exposure of vulnerable objects to the beam-producing light sources.

3. The system of claim 1, wherein the controller coordinates the beams of light to disinfect the at least one volume in space while avoiding interaction of incident and/or reflected light with a detected vulnerable object.

4. The system of claim 3, wherein the vulnerable object is a person or portion of a person.

5. The system of claim 1, wherein the at least one volume requiring disinfection contains or is adjacent to an object to be disinfected and the light beams also disinfect a surface of the object to be disinfected.

6. The system of claim 1, wherein the beam-producing light sources comprise lasers.

7. The system of claim 6, wherein the lasers comprise UV lasers, visible light laser or combinations thereof.

8. The system of claim 1, wherein the light beams comprise incoherent light formed into a beam by subtracting light from at least one direction of the incoherent light and aggregating light in at least one other direction of the incoherent light.

9. The system of claim 1, wherein the at least one light beam is formed by a lens.

10. The system of claim 1, wherein the relative physical positions of the beam-producing light sources and the at least one imaging device are determined by one or more of a user, object detection in the field of view of the at least one imaging device, electromagnetic radiation detected in the field of view of the at least one imaging device and sound detection.

11. The system of claim 1, wherein the relative physical positions of the beam-producing light sources and the at least one imaging device are determined by wireless localization employing wireless signaling devices on the beam-producing light sources and the at least one imaging device, whereby positions and directions of the beam-producing light sources and the at least one imaging device are automatically determined in a region of space by the controller.

12. The system of claim 10, wherein the physical position of one of the beam-producing light sources is used to determine geometric relationship between at least one of the beam-producing light sources and the at least one volume in space.

13. The system of claim 1, wherein the at least one volume in space requiring disinfection is localized from one or more of: detection of objects; detection of orientation of objects; detection of orientation of objects; detection of motions of objects; and, detection of interaction between objects in the field of view of the at least one imaging device.

14. The system of claim 13, wherein the objects are identified by a classifier programmed into the controller or defined by a human operator.

15. The system of claim 13, wherein the object is a human face and the at least one volume in space requiring disinfection is localized from a position of the face, a direction in which the face is pointing and a motion of the face identified as a potential infection-causing motion, whereby the controller is programmed to calculate a dispersion pattern of potentially infective organisms in proximity to the face based on the position of the face, the motion of the face and dispersion tendency of the potentially infective organisms.

16. The system of claim 15, wherein the dispersion pattern includes surfaces of objects that are proximate the face.

17. The system of claim 15, wherein the potential infection-causing motion comprises speaking, a yawn, a cough, a sneeze, a spit, hyperventilation, increased respiratory rate or a deep exhalation.

18. The system of claim 1, wherein the at least one imaging device comprises a plurality of imaging devices and stereo images produced from the collected image data are used to localize the volume in space requiring disinfection.

19. The system of claim 1, wherein the at least one imaging device comprises a plurality of cameras.

20. The system of claim 19, wherein the cameras comprise visible light cameras and/or infrared light cameras.

21. The system of claim 1, further comprising a projector controlled by the controller, the controller programmed to identify whether a person is oriented towards an object that has been disinfected in the at least one volume in space and then to control the projector to project a message onto a surface of the disinfected object or on to a surface of another object adjacent to the disinfected object to indicate that disinfection has been performed.

22. A disinfection system comprising:

a plurality of beam-producing light sources for disinfection;

at least one imaging device for collecting image data in a field of view of the at least one imaging device;

a relationship finder to determine relative physical positions of the beam-producing light sources and the at least one imaging device; and, a programmed controller for controlling the beam-producing light sources based on the image data collected from the at least one imaging device and from known positions and dispersion geometries of the beam-producing light sources, wherein the controller is programmed to:

localize at least one volume in space requiring disinfection;

calculate direction to the at least one volume in space for each available beam-producing light source; and, coordinate at least one light beam projected from the available beam-producing light sources to the at least one volume requiring disinfection to reduce or maintain time required to deliver a threshold disinfecting light dose to the at least one volume in space requiring disinfection, wherein the volumes in space are prioritized as to which ones should be disinfected first and prioritization of the volumes is changed dynamically as new data is acquired in real time, and the controller is programmed to complete an existing disinfection before a new higher priority disinfection unless an assigned priority ranking of the new disinfection exceeds an emergency threshold.

* * * * *